United States Patent [19]

Portal et al.

[11] Patent Number: 4,584,399
[45] Date of Patent: Apr. 22, 1986

[54] PURIFICATION OF L-PHENYLALANINE

[75] Inventors: Charles Portal, Potomac; James F. Walter, Ashton, both of Md.

[73] Assignee: W. R. Grace & Co., New York, N.Y.

[21] Appl. No.: 675,368

[22] Filed: Nov. 27, 1984

[51] Int. Cl.$^4$ ............................................. C07C 45/79
[52] U.S. Cl. .................................................. 562/443
[58] Field of Search ...................................... 562/443

[56]  References Cited

U.S. PATENT DOCUMENTS

| | | | |
|---|---|---|---|
| 3,759,790 | 9/1973 | Nakayama et al. | 562/443 |
| 3,767,528 | 10/1973 | Nagasaki et al. | 562/443 |
| 3,917,511 | 11/1975 | Nakayama et al. | 562/443 |

FOREIGN PATENT DOCUMENTS 960163  9/1982  U.S.S.R. ............................. 562/443

OTHER PUBLICATIONS

Kirk–Othmer, "Encyclopedia of Chem. Tech.", vol. 2, p. 103 (1964).
Jindrich et al., Chem. Abst., vol. 59, #6714g (1960).
Greenstein et al., Chem. of Amino Acids, 1961, 1459.
Samejima, Microbial Prod. of Amino Acids, 1972, 227–59 (CH9).
Neklyudov et al., Khim.–Farm Zh. 1978 (USSR) 12/21–26.
Cogan et al., J. Sci. Food & Agri. 1981, 32/459–66.
Abe et al., Bull. Chem. Soc. Jpn. 1982 (JAPAN) 55/687–89.

*Primary Examiner*—James H. Reamer
*Attorney, Agent, or Firm*—Jill H. Krafte; William W. McDowell, Jr.

[57]  ABSTRACT

A process is disclosed for the separation and recovery of L-phenylalanine from an impure aqueous solution by ultrafiltering and/or centrifuging to remove cellular material and large proteins, contacting the filtered solution with activated carbon to adsorb L-phenylalanine, eluting adsorbed L-phenylalanine, passing the eluate through an ion exchanger, and recovering substantially pure L-phenylalanine from the ion exchange eluate.

27 Claims, No Drawings

PURIFICATION OF L-PHENYLALANINE

BACKGROUND OF THE INVENTION

This invention relates to the purification and recovery of L-phenylalanine (hereinafter "phenylalanine") from an aqueous solution, typically from a microbial fermentation broth. By the method disclosed herein, substantially pure phenylalanine may be selectively recovered from the solution in a single crystallization step, notwithstanding the presence of other amino acids, color bodies, glucose, inorganic salts, extracellular proteins, organic acids, etc., in the original solution.

Phenylalanine traditionally has been difficult to purify from fermentation broths. The presence of inorganic salts, particularly those characteristic of precursor-based broths, renders separation by ion exchange inefficient. Alkali salts typically will be present which cannot be removed by conventional ion exchange methods without incurring a 20 to 30% phenylalanine loss unless multistep fractional crystallization or inefficient elution displacement techniques are used.

Under certain conditions, activated charcoal has been used to adsorb phenylalanine or a substituted phenylalanine from a culture broth. Examples of these uses are found in U.S. Pat. No. 3,759,790 and U.S. Pat. No. 3,917,511 (Nakayama et al.), which disclose mixture with active carbon and elution, followed by passage through a column of strongly acidic cation exchange resin. U.S. Pat. No. 3,767,528 (Nagasaki et al.) discloses adsorption of 3,4-dimethoxyphenyl-L-alanine on active charcoal and eluting with water as the first step of a four-cystallization recovery. Greenstein et al., "Chromatography", Chemistry of Amino Acids, p. 1459 (1961), describes a sequence of events employed in the separation of amino acids from a protein hydrolysate, in which aromatic amino acids were adsorbed on charcoal and the resulting effluent was passed through a series of ion exhanges to yield individual amino acids.

SUMMARY OF THE INVENTION

A simplified method for obtaining pure crystals of phenylalanine from an aqueous solution has been discovered. When a phenylalanine-containing solution is ultrafiltered for removal of cell mass, large proteins, etc., and contacted with activated carbon, the carbon selectively adsorbs phenylalanine, color bodies and glucose, and rejects inorganic salts and non-aromatic amino acids. Changes in effluent pH indicate when the loading capacity of the activated carbon has been reached. Phenylalanine can be selectively eluted from the carbon with suitable solvents. The phenylalanine-containing eluate is passed through an ion-exchanger to eliminate remaining impurities and/or to concentrate the eluate from the carbon adsorption step. The application of this series of steps to a highly contaminated phenylalanine solution allows the attainment of phenylalanine crystals of high purity in high yields using a single, conventional crystallization step.

It is the primary object of this invention to substantially simplify the overall phenylalanine purification and recovery process by avoiding multistage fractional crystallization.

Moreover, it is desired to obtain a product of considerable purity using a single crystallization step.

It is further object to provide an economical means of recovering phenylalanine which otherwise might be lost in process wastestreams.

DETAILED DESCRIPTION OF THE INVENTION

The simplified separation and recovery method described herein will find its greatest utility in the removal of phenylalanine from aqueous solutions which contain phenylalanine precursor compounds in the form of salts. The method additionally will be useful for the recovery of phenylalanine from a variety of other aqueous solutions which contain impurities. The process might, for example, be used as the primary process for recovery of phenylalanine from fermentation broths or other processing liquids. Alternatively, it may be used as an adjunct to a conventional phenylalanine purification process for recovery of the phenylalanine from the process wastestream.

Briefly, a method of separating phenylalanine from an aqueous solution which comprises phenylalanine, cellular material, inorganic salts and organic compounds is disclosed in which cellular material and proteins, if present, are removed from the aqueous solution. This may be done by ultrafiltration and/or centrifugation. The resulting solution then is contacted with activated carbon, the activated carbon is separated from the solution and phenylalanine is eluted from the activated carbon. The phenylalanine-comprising eluate is passed through an ion exchanger and phenylalanine is eluted from the ion exchange resin. Substantially pure phenylalanine is recovered from the eluate by a single crystallization.

The preferred embodiment, described herein, is for the recovery of phenylalanine from a microbial fermentation broth. The broth preferably is clarified by ultrafiltration to remove microorganisms and proteins, although centrifugation may be employed for this purpose, if desired. If ultrafiltration is used, the molecular weight ("MW") cutoff should be about 5,000 to 1,000,000, oreferably about 100,000, depending on the type of impurities present. It normally will not be necessary to use a filter with a lower MW cutoff, as the broth typically will comprise large particles which will be filtered and much smaller molecules, peptides, for example, which cannot efficiently be removed from the broth in this manner. In this perferred embodiment, the ultrafilter is coupled with centrifugation in a closed loop operation for optimum clarification of the broth. For convenience, the phenylalanine-containing solution resulting from this step will be referred to as the "filtered" broth or solution, regardless of the actual clarification method utilized.

The filtered broth will contain a variety of impurities from which the phenylalanine must be separated. The principal contaminants will be the components of the fermentation media itself, unreacted phenylalanine precursor, other amino acids which may have been produced, and color bodies. Color bodies, which include lipids, peptides and other proteins sufficiently small to pass through the ultrafiltration or centrifugation step, are excreted by microorganisms during fermentation.

The media components will comprise a carbon source (e.g., glucose, corn steep liquor, etc.), nitrogen source (e.g., ammonium salts of organic or inorganic acids), various inorganic elements (e.g., potassium phosphate or magnesium sulfate), and vitamins (e.g., biotin or thiamine). In addition, the fermentation broth may contain unreacted phenylalanine precursor (phenylpyruvic acid, for example), which may be present in the form of an alkali or sodium salt.

The filtered phenylalanine-containing solution is contacted with activated carbon for the selective adsorption of phenylalanine from the environment just described. Glucose, phenylalanine precursor (e.g., phenylpyruvic acid) and color bodies compete with phenylalanine for adsorption sites on the activated carbon. Other aromatic amino acids, tryptophan, for example, also will be adsorbed if present in the solution. However, the remaining impurities either are not adsorbed at all or are adsorbed to a very minor degree. Therefore, this carbon adsorption step will serve to separate the phenylalanine from such impurities as non-aromatic amino acids, salts and other compounds which may have been present in the media or solution.

The carbon adsorption step is particularly advantageous where the solution comprises a high level of salts. Salts may be present as growth media constituents, e.g., potassium phosphate, or as precursor salts, e.g., potassium or sodium phenylpyruvic acid. The presence of these salts would make direct separation by ion exchange ineffective or inefficient, due to competition for sites on the resin. The selective adsorption of phenylalanine on the activated carbon affords a simple and an efficient means of desalting the phenylalanine solution. This step is similarly advantageous where the solution comprises high levels of undesired amino acids.

Most commercial grades of activated carbon or charcoal will be suitable for use in this separation method. Carbon from different sources—i.e., wood, coal, rice hulls—will have slightly different properties and some may be more desirable in certain situations. A key characteristic related to suitability for this process will be high surface area, with surface areas of about 1,000 to about 1,500 square meters per gram of carbon being preferred. Additionally, molasses numbers of about 400 or greater may be preferred.

The preferred size of the activated carbon particles will be dependent, in part, on the design and mode of operation of the adsorption system. To this extent, selection of the appropriate particle size will be within the skill of the designer of the recovery system. However, in terms of adsorption efficiency it is preferred that the particles be as small as practicable. Reducing the particle size, thereby creating a larger surface area per unit weight of carbon, increases the carbon's adsorption capacity. Thus, although granular activated carbon (carbon with particle size in the range of about 12×40 or even larger) is suitable for use in this process, pulverized activated carbon (about 80 mesh) has a greater adsorption capacity per unit weight of carbon.

Regardless of increased adsorption efficiency with pulverized activated carbon, however, its use may pose some drawbacks for the overall recovery process. For example, carbon dust may cause plugging of back flush screens. In addition, attrition losses may cause loss of adsorbed phenylalanine and downstream contamination of the eluted phenylalanine product, or both, depending on the process stage during which the attrition loss occurs. Any displaced carbon must be filtered out prior to crystallization. These potential problems may be alleviated by washing the activated carbon prior to use in this process, and/or using of filters to eliminate attrition losses.

It is preferred to pretreat the activated carbon with acid before employing it for phenylalanine adsorption. In the case of new activated carbon, treatment with a strong acid will clean the carbon and will tend to leach out some of the ash content which may be present. This will avoid contamination of the phenylalanine by slow leaching of the ash during the adsorption and elution cycles. In the case of carbon which already has gone through one or more adsorption-elution cycles, acid pretreatment may be used to more fully regenerate the carbon.

For convenience and effectiveness, sulfuric acid will be preferred; 1.5 N sulfuric acid is suitable. Other acids, e.g., hydrochloric, phosphoric, nitric, may be used. The pre-treatment most advantageously comprises running about two bed volumes of acid (pH of about 3 to about 4) over the carbon. The acid pretreatment preferably should be followed by rinsing with water or with a mildly basic solution prior to use in the carbon adsorption step of this process so that the carbon surface is near neutral to slightly basic. By raising the pH of the carbon surface in this manner, co-adsorption of other carboxylic acid impurities present in the broth can be minimized.

The pH of the phenylalanine-containing solution will affect the selectivity of the adsorption, although it does not appear that pH variation has a significant effect on the levels of phenylalanine adsorbed. However, at very low solution pH, i.e., less than about 2 to 3, significant amounts of glutamic acid, glycine, valine and leucine also may be adsorbed. At pHs of about 3.5 to 4.5, salts are adsorbed. Thus, to increase the preferential adsorption of phenylalanine over other amino acids and salts, the pH should be about 5.0 to 6.0 or higher. A pH of about 5.5 to about 6.5 is optimal for the selective separation of phenylalanine, as compared with other amino acids and salts. At elevated pHs, above about 10 to about 11, it is possible to separate color bodies from the desired phenylalanine by a semi-chromatographic operation of the carbon columns, since the adsorption of color bodies is greatly decreased at these elevated pHs.

The carbon adsorption step of the phenylalanine recovery process of this invention may be carried out in either a batch or continuous process reactor. For commercial expediency, a packed column operating with continuous throughput is preferred. Because phenylalanine is selectively adsorbed, the carbon bed of this process may be very compact. The adsorption capacity of activated carbon is about 0.05 to about 0.25 grams phenylalanine per gram of carbon, preferably at least about 0.15 to about 0.2 grams phenylalanine per gram of carbon. Once the adsorption capacity of the selected carbon is determined, the precise design, size and residence time of the carbon adsorption reactor will be within the knowledge and skill of the designer.

Provisions may be made for periodic removal of saturated activated carbon from the upstream portion of the column, if moving bed units are used instead of packed towers. The adsorption capacity of the saturated activated carbon may be at least partially regenerated by eluting as described below, and the regenerated, activated carbon returned to the downstream portion of the column. In a batch or a packed column process, the entire complement of activated carbon may be regenerated for re-use by eluting in the same manner. If a phenylalanine-selective eluent, such as ethyl acetate, is used, regeneration of the carbon by washing with a strong caustic, such as sodium hydroxide or potassium hydroxide, may be required. The acid pretreatment described above also may be used to enhance regeneration of the adsorptive activity of the carbon.

The purification and recovery process disclosed herein may be conducted at any convenient temperature compatible with maintaining the integrity of the phenylalanine. Temperatures in the 25° to 75° range are suitable. In most cases, the phenylalanine-containing feed stock will be at or near fermentation temperatures, that is, about 20° C. to about 45° C. There is no need to maintain this elevated temperature, and the adsorption can be conducted at or near room temperature, since a change in temperature merely causes a shift in the adsorption curve, rather than alteration of adsorption capacity.

The phenylalanine-containing solution and the activated carbon are contacted in the reaction vessel, preferably for a sufficient length of time for the adsorption reaction to reach equilibrium or saturation. The equilibrium point can be ascertained by assaying the solution or effluent for free phenylalanine. Alternatively, pH may be used as an equilibrium indicator. There is a substantial initial increase in pH of about 1.5 to 2.5 pH units as acids are adsorbed on the activated carbon. The pH then gradually falls approximately to the initial or inlet pH. The gradual drop in pH indicates some phenylalanine bleedthrough as the adsorption sites on the carbon begin to fill up. The leveling-off of the pH approximately to the initial level indicates equilibrium, or saturation of the carbon. Because of the phenylalanine bleedthrough prior to saturation, it is preferred to use multiple columns or to recycle the effluent through multiple passes until the saturation point is reached. Continuous pH monitoring in this manner will provide an anticipatory means for determining when the column is approaching saturation.

For purposes of detecting peak loading, or saturation, of phenylalanine onto the activated carbon, the "initial pH" is defined as the pH of the aqueous solution at or immediately prior to contacting the activated carbon and the aqueous solution. A decrease "approximately to initial pH" means a decrease in pH levels to or close to the starting or pre-contact pH.

Phenylalanine may be eluted from the activated carbon at any time, preferably when the carbon has become saturated. In an embodiment utilizing a batch reactor, the elution step may be performed after one or more batches have been processed. In an embodiment utilizing a continuous column reactor, the whole column may be flushed with eluent. Alternatively, saturated or substantially saturated activated carbon may be removed periodically from the upstream portion of the column, washed with eluent and returned to the column.

The elution may be conducted at any desired temperature between about 25° and 70° C. Slightly elevated temperatures, about 50° to about 60° C., may be desired for the increased phenylalanine solubility they afford. This choice will depend on the relative economics of each situation since temperature is not critical in this step. A variety of solvents are suitable for use in the carbon elution step of this process. For example, water, aqueous ammonia, tetrahydrofuran and low molecular weight acetates, alcohols and ketones (e.g., acetic acid, ethyl acetate, methanol, ethanol, isopropanol, acetone) all are suitable for elution of adsorbed phenylalanine from activated carbon. The selection of the solvent for this elution is a process choice which will depend on the overall process design. Solvents such as those indicated above exhibit some variability in terms of the concentration of the resulting phenylalanine-containing stream and in terms of the selectivity of the elution. For example, the use of water, preferably deionized, or aqueous ammonia will result in a relatively dilute phenylalanine stream which is not contaminated by the co-elution of color bodies. If aqueous ammonia is used, it may be at pHs of about 9 to about 13, preferably about pH 12 for the most effective phenylalanine elution.

Alternatively, the carbon adsorption step itself may be utilized for concentration as well as separation. If this is desired, a solvent such as tetrahydrofuran or low molecular weight acetates, alcohols or ketones is preferred, with ethyl acetate being the most preferred. The elution of phenylalanine will occur in a concentrated band when one of these solvents is used, eliminating the need for further processing of large volumes of solution. However, some organic impurities will co-elute with the phenylalanine and these must be removed before crystallization.

The phenylalanine-eluent solution next may be passed through an ion exchange system for further polishing. Ion exchange is most effective when conducted after the activated carbon treatment since salts present in the initial phenylalanine-containing solution are removed in the carbon adsorption step. Where a high purity phenylalanine product is desired, this ion exchange step may be used to remove organic impurities which may remain after elution of phenylalanine from the carbon. These impurities may impart color to the final product and may act as nucleation inhibitors in the crystallization process. The polishing function is important where the activated carbon eluent is one which co-elutes color bodies along with the phenylalanine. In addition, glucose present in the initial phenylalanine-containing solution will be separated from the phenylalanine when the solution is passed through the ion exchange system.

Where the carbon elution solvent is water or ammonia, the dilute phenylalanine stream can be concentrated (e.g., by evaporation or reverse osmosis) before crystallization, or the ammonia can be evaporated in order to send an aqueous stream to an ion exchanger for further polishing. Another option, depending on the degree of contamination of the broth and the nature and strength of the solvent used in the carbon elution step, would be to pass rediluted eluate through an ion exchanger containing a cationic resin in the hydrogen or ammonia form. The latter, in addition to eliminating impurities, will produce a concentrated stream going to the crystallizer. It should be noted that removal of the solvent used in the carbon elution step prior to ion exchanger is optional.

An ion exchange resin must be selected which is compatible with the activated carbon eluent. That is, the resin should be insoluble in the carbon elution solvent. Moreover, the resin should have good structural integrity. That is, it should be resistant to expansion and swelling on exposure to the solvent, which could lead to breakage of the resin. For maximum resistance, a highly crosslinked resin, that is, a resin with about 10 to 20 percent crosslinking, should be used. A suitable example is 20% divinyl benzene. It has been found that Amberlite 200 (TM) (Rohm & Haas), a strongly acidic microporous resin, is particularly suitable when ethyl acetate or ammonia is used as the solvent in the carbon elution step. The selection of the ion exchange resin will be within the knowledge and skill of the process designer.

The ion exchange process requires the phenylalanine-containing feed—that is, the eluate from the carbon adsorption step—to be acidified. This causes the phenylalanine to be protonated so that ion exchange will be effective. The pH of the feed to the ion exchange column(s) should be adjusted to about 1.0 to about 4.0, referably about 1.5 to about 2.5. The pH actually selected will depend on the ion exchange resin used in the column(s).

Prior to elution, the phenylalanine-saturated ion exchange column is washed with water or, more preferably, with fresh solvent, e.g., ethyl acetate, to displace any adsorbed impurities. A simple water wash may not be sufficient to displace the impurities from the pores of the resin. The solvent wash may be followed with a water wash.

Elution of the phenylalanine from the ion exchange column(s) may be with any base. Due to its volatility, an ammonia solution will be preferred. The concentration of the ammonia solution may be varied. For example, a concentrated eluent stream is very effective in displacing the phenylalanine from the column. However, there may be some difficulty in separating the ammonia from the phenylalanine product after elution and for this reason it is preferred to use a dilute ammonia solution which more easily can be removed. It has been found that by raising the temperature of the eluent to about 30° to 60° C. dilute ammonia is as effective an eluent as concentrated ammonia. Using the eluent at these elevated temperatures, concentrations of about 0.3 to about 3.0 weight percent of ammonia will be satisfactory.

The phenylalanine is recovered from the purified solution, typically by conventional crystallization procedures. Using the purification and recovery process described above, a phenylalanine product of high purity, e.g., 90 to 100% pure, may be obtained with a single crystallization step. By virtue of the complementary selectivities of the steps outlined above, a product of the indicated purity is possible without resort to multiple crystallization.

To summarize, by using ultrafiltration and/or centrifugation, large organic molecules and cellular materials can be stripped from the phenylalanine containing broth or solution. The filtered broth is then contacted with activated carbon, where the selectivity of the adsorption of phenylalanine onto the carbon allows for its effective separation from salts, undesired amino acids and other contaminants. The desalted phenylalanine-containing eluate then may be passed through an ion exchanger for final purification and/or concentration without contamination or "blinding" by the salts. The concentrated product stream from the ion exchanger will comprise substantially pure phenylalanine, from which substaltially pure crystals of phenylalanine may be made in a single crystallization.

The process of this invention may be used as the primary purification and recovery of phenylalanine from, e.g., fermentation broths. Alternatively, it may be desired to use conventional techniques for primary recovery and use this process to recover phenylalanine remaining in the mother liquor of the conventional process.

The examples which follow are given for illustrative purposes and are not meant to limit the invention described herein. The following abbreviations have been used throughout in describing the invention:

°C.—degree(s) Centigrade
DI—de-ionized
$ft^2$—square foot
gal—gallons(s)
gm—gram(s)
HPLC—high pressure liquid chromatography
hr—hour(s)
kg—kilogram(s)
l—liter(s)
lb—pound(s)
M—molar
meq—milliequivalents
mg—milligram(s)
min—minute(s)
ml—milliliter(s)
MW—molecular weight
N—normal
%—percent
psi—pounds per square inch
RPM—revolutions per minute
TLC—thin layer chromatography

EXAMPLE I (Complete Purification Process)

Phenylalanine was recovered by the following process from a fermentation broth containing 22.6 gm/l phenylalanine, 1.13 gm/l phenylpyruvate, 15.0 gm/l glucose and 10.0 percent solids on a volume basis. The broth was ultrafiltered by passage through an Amicon H5P100-43 (100,000 MW cut-off) hollow fiber ultrafiltration unit (Amicon Corporation). The recirculation rate on the unit was 20.6 l/min with an average pressure drop of 10.0 psi. An average permeation rate of 7.0 gal/$ft^2$-day was observed.

A column was filled with 500.0 gm Westvaco Nuchar WV-G 12×40 (TM) activated carbon (Westvaco Corporation) which previously had been activated by contact with 259.0 gm concentrated sulfuric acid followed by a water wash to raise the effluent pH to 3.6. The ultrafiltered broth was loaded onto the carbon column at 57.0 ml/min. After 6.0 liters of broth had passed through the column, phenylalanine breakthrough was observed and the flow was stopped. The column was washed with 1.0 liter of DI water and eluted with 9.0% ethyl acetate at 60° C. and 50.0 ml/min. A total of 88.0 gm phenylalanine (measured by HPLC) was recovered in 6.0 liters of eluate. Two liters of this phenylalanine-containing effluent were processed further by ion exchange.

An ion exchange column was prepared by placing 220.0 ml of Amberlite 200 (TM) (Rohm and Haas) ion exchange resin in a column. The resin was converted to the $NH_4{}^+$ form by washing with 500.0 ml 30% ammonium hydroxide. Color was released from the resin. The resin then was washed with DI water to lower the effluent pH to 9.1. The pH of the two liters of phenylalanine-containing eluate from the carbon column above was adjusted to 1.8 with concentrated sulfuric acid. The phenylalanine-containing eluate then was passed through the ion exchange column at a rate of 10.0 ml/min. Phenylalanine breakthrough was observed after 1750.0 ml solution had been passed through the bed and flow was stopped at that point. The column was washed with 280.0 ml DI water and was eluted with 1.0 liter of 29% ammonium hydroxide. The eluate was analyzed by HPLC and found to contain a total of 20.0 gm.

The phenylalanine-containing eluate from the ion exchange step was pH adjusted to 7.0 with concentrated sulfuric acid and loaded into a crystallizer heated to 60° C. and a vacuum applied through an aspirator. A total of 16.0 gm crystals was obtained. The crystalline product was analyzed by titration and found to be 98% phenylalanine. An optical rotation of −33.1° was measured.

EXAMPLE II (Variation in Particle Size of Activated Carbon)

Six granular samples and one pulverized sample of activated carbon were examined. Five grams of each carbon were washed with 50.0 ml water and were added to 50.0 ml of a phenylalanine-containing feed broth whose amino acid and glucose composition is indicated in TABLE A. Each sample was agitated for 3.0 hours at room temperature. The carbon was filtered out, and the samples of the remaining broth were analyzed by HPLC. The results are shown in TABLE A.

loaded (not always to capacity) with 1.0 liter of the feed broth used in Example II. Following loading, the columns were washed with one bed volume of water to remove excess solution. Phenylalanine was eluted from the activated carbon with 1.0 liter of the eluents listed in TABLE B. The eluate was analyzed by HPLC for phenylalanine. The results are shown in TABLE B.

TABLE B

| | | (Variation of Eluent) | | | | |
|---|---|---|---|---|---|---|
| Eluent | Column Size[2] | PHE[1] Load[2] | PHE[1] Removed[2] | Recovery[3] | Concentration[4] | Maximum Concentration[4] |
| NH$_3$/H$_2$O (pH 11) | 82 | 12.00 | 7.50 | 62.00 | 3.75 | 4.50 |
| NH$_3$/H$_2$O (pH 12) | 82 | 12.00 | 6.90 | 60.00 | 6.90 | 9.50 |
| | | | 10.60 | 90.00 | 4.30 | 9.50 |
| NH$_3$/H$_2$O (pH 13) | 42 | 5.20 | 3.50 | 70.00 | 3.50 | 12.50 |
| Deionized H$_2$O (80° C.) | 43 | 7.50 | 4.00 | 53.00 | 4.00 | 8.50 |
| | | | 6.80 | 90.00 | 1.50 | 8.50 |
| 30% Ethanol | 45 | 6.70 | 5.25 | 81.00 | 5.25 | 10.00 |
| 50% Methanol | 78 | 11.00 | 5.73 | 52.00 | 7.20 | 10.00 |
| 70% Methanol | 80 | 12.10 | 8.08 | 73.50 | 10.10 | 16.20 |
| | | | 10.80 | 90.00 | 7.10 | 16.20 |
| 75% Isopropanol | 82 | 11.25 | 7.40 | 66.00 | 7.40 | 12.20 |
| | | | 10.10 | 90.00 | 5.00 | 12.20 |
| 10% THF | 48 | 7.00 | 5.50 | 75.00 | 16.00 | 21.70 |
| | | | 6.50 | 90.00 | 10.10 | 21.70 |
| 9% Ethyl Acetate | 47 | 6.90 | 5.20 | 75.00 | 17.30 | 24.20 |
| | | | | 6.22 | 90.00 | 12.50 | 24.20 |

[1]Phenylalanine
[2]grams
[3]percent (grams/grams)
[4]Concentration of phenylalanine

EXAMPLE IV (Pattern of Adsorption and Elution of Phenylalanine in Activated Carbon Step)

A 500 gm carbon column was set up, containing Nuchar (TM) WV-G activated carbon (Westvaco Corporation). The carbon column was prepared by washing with concentrated sulfuric acid followed by a water wash to raise the pH to 3.0.

A fermentation broth comprising 22.3 g/l phenylalanine (89 gm total phenylalanine) was selected which also comprised the amino acids glutamine, glycine, alanine, proline, leucine and lysine, as well as culture

TABLE A

| | | (Variation In Particle Size of Activated Carbon) | | | | | | | | |
|---|---|---|---|---|---|---|---|---|---|---|
| Feed Carbon | Particle Size | GLU[1] 1.70[11] | GLY[2] 0.76 | ALA[3] 4.60 | PRO[4] 0.52 | VAL[5] 0.43 | PHE[6] 12.30 | ILE[7] 0.46 | LEU[8] 0.23 | LYS[9] 0.46 | Gl.[10] 6.50 |
| Calgon CAL[12] | 12 × 40 | 1.60 | 0.73 | 4.50 | 0.52 | 0.48 | 1.23 | 0.13 | 0.22 | 0.49 | 4.10 |
| Calgon CPG[12] | 12 × 40 | 1.58 | 0.71 | 4.30 | 0.53 | 0.47 | 1.32 | 0.13 | 0.22 | 0.49 | 4.18 |
| Calgon APC[12] | 12 × 40 | 1.40 | 0.73 | 5.60 | 0.52 | 0.60 | 1.40 | 0.16 | 0.22 | 0.50 | 4.12 |
| Nuchar (TM)WV-B[13] | | 1.50 | 0.71 | 4.20 | 0.52 | 0.45 | 1.78 | 0.14 | 0.23 | 0.46 | 4.09 |
| Nuchar (TM)WV-G[13] | 12 × 40 | 1.60 | 0.74 | 4.40 | 0.54 | 0.47 | 1.34 | 0.13 | 0.23 | 0.48 | 3.91 |
| Calgon NAP[12] | | 1.70 | 0.73 | 5.50 | 0.60 | 0.60 | 1.04 | 0.17 | 0.23 | 0.56 | 4.20 |
| Calgon BL[12] | Pulverized | 1.63 | 0.72 | 4.54 | 0.51 | 0.49 | 0.58 | 0.13 | 0.22 | 0.49 | 3.75 |

[1]Glutamic Acid
[2]Glycine
[3]Alanine
[4]Proline
[5]Valine
[6]Phenylalanine
[7]Isoleucine
[8]Leucine
[9]Lysine
[10]Glucose
[11]All entries are grams per liter.
[12]Calgon Corporation
[13]Westvaco Corporation

EXAMPLE III (Variation of Eluent for Carbon Adsorption Step)

Columns were filled with Calgon APC 12×40 (TM) (Calgon Corporation) as indicated in TABLE B, and medium and cellular material. The broth was ultrafiltered by passage through a 100,000 MW ultrafiltration membrane (Amicon Corporation) and the pH was adjusted to 4.85 with concentrated sulfuric acid.

The filtered broth was loaded onto the column at 50 ml/min., followed by one liter of water to wash the column. The effluent was collected in 500 ml cuts and analyzed by thin layer chromatography (TLC) to detect amino acids. No phenylalanine was observed in the effluent until 3.0 liters had passed through the column. Even after 4.5 liters, the effluent had a phenylalanine concentration of only 4.2 gm/l, indicating that most of the phenylalanine was being adsorbed onto the carbon. Throughout the loading cycle, none of the other amino acids was adsorbed to any significant extent, as indicated by fairly constant effluent levels approximating the respective initial levels of each amino acid in the broth. From the effluent analysis, it was determined that 82 grams of phenylalanine were adsorbed onto the carbon. This corresponds to about 92% of the total phenylalanine present in the broth and to a loading of 0.16 gm phenylalanine per gram of carbon.

Following loading, the carbon was eluted with 5.5 liters 9% ethyl acetate at 50.0 ml/min. and the effluent collected in 500 ml cuts. The column was washed with 1000.0 ml DI water to displace the remaining eluent. The phenylalanine came through in a tight band of about 4.0 liters with a maximum concentration of 29 gm/l and an average concentration (at 93% recovery) of 19 gm/l. This band contained over 76 gm phenylalanine, or 85.4% of the total phenylalanine present in the broth.

It was noted that color bodies co-eluted with the phenylalanine. Through the first 2.0 liters of elution, the eluent had a light yellow color. This color increased to tan at about 4.0 liters and decreased almost to colorless at the end of the elution.

Eluent cuts that contained more than 3.0 gm/l were vacuum crystallized in three batches. The crystals were washed with 5 ml acetone per gm wet crystals and dried. The mother liquor from each batch was added to the next batch. A total of 66.2 gm dry raw phenylalanine was collected. The product had an off-white color and was by titration and found to be 94% phenylalanine.

EXAMPLE V (Variation of Ion Exchange Resins)

Ion exchange columns were set up (nominal volume 72.0 to 200.0 ml) containing one of the four resins listed in TABLE C. All resins were converted to the H+ form by washing each column with one liter of 1.0 M sulfuric acid followed by several liters of water. To each column, ethyl acetate containing effluent from carbon columns as described in Example I (pH adjusted to 1.5 with sulfuric acid) was loaded at a rate of 5.0 ml/min. The columns then were washed with 150.0 to 500.0 ml DI water and eluted with 2.0 M ammonium hydroxide solution at 5.0 ml/min. The results, shown in TABLE C, indicate that the weakly acidic resins (IRC-84 and IRC-50) did not pick up phenylalanine and showed signs of deterioration. The strongly acidic resins (IRC-120 and Amberlite 200 (TM)) showed considerable pickup, although IRC-120 showed signs of deterioration.

TABLE C

| Resin[1] | (Variation in Ion Exchange Resin) | |
|---|---|---|
| | PHE Capacity[2] | Condition |
| IRC-84 | 0.00 | Gray discoloration |
| IRC-50 | 0.00 | Yellow-green discoloration |
| IRC-120 | 0.40 | Yellow discoloration and swelling |
| Amberlite 200 | 0.44 | White |

[1] All resins from Rohm & Haas
[2] Phenylalanine measured in meq/ml.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. A method of separating L-phenylalanine from an aqueous solution comprising L-phenylalanine, cellular material, inorganic salts and organic compounds, comprising
   (a) removing cellular material and proteins from said aqueous solution,
   (b) contacting the resulting solution with activated carbon,
   (c) separating said activated carbon from the solution,
   (d) eluting L-phenylalanine from said activated carbon with water, aqueous ammonia, tetrahydrofuran or ethyl acetate,
   (e) passing the L-phenylalanine-comprising eluate through an ion exchanger, and
   (f) eluting L-phenylalanine from the ion exchange resin.

2. The method of claim 1 in which substantially pure L-phenylalanine is recovered from the eluate of step (f) by a single crystallization.

3. The method of claim 1 in which cellular material and proteins are removed from said aqueous solution in step (a) by ultrafiltration or centrifugation.

4. The method of claim 1 in which said cellular material and proteins are removed by ultrafiltration in closed loop operation with centrifugation.

5. The method of claim 3 in which said ultrafiltration removes particles with a molecular weight cutoff of about 5,000 to about 1,000,000.

6. The method of claim 1 in which said activated carbon has a high surface area.

7. The method of claim 6 in which said activated carbon has a surface area of about 1,000 to about 1,500 square meters per gram of carbon.

8. The method of claim 1 in which said activated carbon is pre-treated by washing with an acidic solution comprising an acid selected from the group comprising sulfuric, hydrochloric, phosphoric and nitric acids.

9. The method of claim 8 in which said activated carbon is washed with water or a mildly basic solution following pretreatment with said acidic solution.

10. The method of claim 1 in which the pH of the solution in step (b) is at least about 5.0.

11. The method of claim 1 in which said aqueous solution and said activated carbon are contacted for a period sufficient for the carbon adsorption reaction to reach equilibrium or saturation.

12. The method of claim 1 in which said aqueous solution and said activated carbon are contacted for a period sufficient to allow the solution pH to increase substantially and then to fall to approximately the initial pH.

13. The method of claim 12 in which the solution pH increases by about 1.5 to about 2.5 pH units.

14. The method of claim 1 in which the carbon adsorption of steps (b) and (c) comprises multiple carbon columns or means for recycle of the effluent through multiple passes.

15. The method of claim 1 in which the solvent in elution step (d) is aqueous ammonia with a pH of about 9 to about 13.

16. The method of claim 1 in which the activated carbon may be regenerated for recycle.

17. The method of claim 16 in which regeneration of said activated carbon includes washing with a strong acid or with a strong caustic.

18. The method of claim 1 in which the resin of said ion exchanger of step (e) is a strongly acidic, cationic resin with about 10 to about 20 percent crosslinking.

19. The method of claim 1 in which the resin of said ion exchanger is compatible with the eluent used in step (d).

20. The method of claim 1 in which the L-phenylalanine-comprising eluate of step (e) is acidified prior to passage through an ion exchanger.

21. The method of claim 20 in which the pH of the acidified eluate is less than about 4.0.

22. The method of claim 1 in which the eluent used in step (d) is deionized water or aqueous ammonia, said ammonia, if present, is removed from the phenylalanine-comprising eluate, and the resulting phenylalanine-comprising aqueous solution is passed through an ion exchanger, said ion exchanger characterized in that it causes the phenylalanine-comprising solution downstream of said exchanger to be substantially more concentrated than the phenylalanine-comprising solution upstream of said exchanger.

23. The method of claim 1 in which the eluent used in step (d) is tetrahydrofuran or ethyl acetate and the phenylalanine-comprising eluate is passed through an ion exchanger, said ion exchanger characterized in that (1) the resin is compatible with the eluent selected in step (d), and (2) said resin is capable of selectively adsorbing phenylalanine without significant co-adsorption of color bodies or other impurities.

24. The method of claim 1 in which the eluent used in step (f) is an aqueous ammonia solution.

25. The method of claim 24 in which said aqueous ammonia solution is about 0.3 to about 3.0 weight percent ammonia and is at about 30° to about 60° C.

26. A method for separating L-phenylalanine from an aqueous solution comprising L-phenylalanine, inorganic salts and organic compounds, comprising:
 (a) contacting said solution with activated carbon,
 (b) separating said activated carbon from said solution,
 (c) eluting L-phenylalanine from said activated carbon with water, aqueous ammonia, tetrahydrofuran or ethyl acetate,
 (d) passing the L-phenylalanine-comprising eluate through an ion exchanger, and
 (e) eluting L-phenylalanine from the ion exchange resin.

27. The method of claim 26 in which substantially pure L-phenylalanine is recovered from the eluate of step (e) by a single crystallization.

* * * * *